US006410705B1

(12) United States Patent
Ziegler et al.

(10) Patent No.: US 6,410,705 B1
(45) Date of Patent: Jun. 25, 2002

(54) NUCLEOTIDE SEQUENCES CODING FOR THE THRE GENE AND PROCESS FOR THE ENZYMATIC PRODUCTION OF L-THREONINE USING CORYNEFORM BACTERIA

(75) Inventors: Petra Ziegler, Aachen; Lothar Eggeling; Hermann Sahm, both of Jülich; Georg Thierbach, Bielefeld, all of (DE)

(73) Assignee: Degussa Huls Aktiengesellschaft, Hanau ( * ) Notice: Subject to any disclaimer, the term of this patent is extended or adjusted under 35 U.S.C. 154(b) by 0 days.

(21) Appl. No.: 09/431,099

(22) Filed: Nov. 1, 1999

(30) Foreign Application Priority Data

Sep. 1, 1999 (DE) .......................... 199 41 478

(51) Int. Cl.[7] .................. C07H 21/04; C12N 15/74; C12N 1/20; C12N 9/10; C12P 13/08
(52) U.S. Cl. .............. 536/23.2; 435/320.1; 435/252.32; 435/193; 435/115
(58) Field of Search ...................... 536/23.2; 435/320.1, 435/252.32, 193, 115

(56) References Cited

FOREIGN PATENT DOCUMENTS

| DE | 198 31 609 | 4/1999 |
|----|------------|--------|
| EP | 0 318 663 | 6/1989 |
| EP | 0 593 792 | 4/1994 |
| EP | 0 887 420 | 12/1998 |
| EP | 0 108 790 | 6/2001 |
| WO | WO 88 09819 | 12/1988 |
| WO | WO 93 09225 | 5/1993 |
| WO | WO 01 00805 | 1/2001 |
| WO | WO 01 00843 | 1/2001 |

OTHER PUBLICATIONS

Eikmanns B J et al: "Molecular aspects of lysine, threonine, and isoleucine biosynthesis in Corynebacterium glutamicum", Antonie Van Leeuwenhoek, Dordrecht, NI., Bd. 64, Nr. 2, 1993, p. 145–163, XP000918559.

Molenaar D et al.: "Biochemical and genetic characterization of the membrane-associated malate dehydrogenase (acceptor) from Corynebacterium glutamicum", European Journal of Biochemistry, Berlin, DE., Bd. 254, 1998, p. 395–403, XP000941422.

Abstract of JR above.

Abstract of OR above.

*Primary Examiner*—Rebecca E. Prouty
*Assistant Examiner*—David J Steadman
(74) *Attorney, Agent, or Firm*—Pillsbury Winthrop LLP (57) ABSTRACT

The invention relates to preferably recombinant DNA derived from Corynebacterium and replicable in coryneform microorganisms, which contains at least one nucleotide sequence that codes for the thrE gene, and a process for the production of L-threonine.

11 Claims, 2 Drawing Sheets

NUCLEOTIDE SEQUENCES CODING FOR THE THRE GENE AND PROCESS FOR THE ENZYMATIC PRODUCTION OF L-THREONINE USING CORYNEFORM BACTERIA

CROSS REFERENCE TO RELATED APPLICATIONS

The present application claims priority under 35 U.S.C. §119 to German application 199 41 478.5, filed on Sep. 1, 1999.

BACKGROUND OF THE INVENTION

1. Field of the Invention

The present invention relates to nucleotide sequences coding for the thrE gene and a process for the enzymatic production of L-threonine using coryneform bacteria, in which the thrE gene is amplified.

2. Background Information

L-threonine is used in animal nutrition, in human medicine and in the pharmaceutical industry.

It is known that L-threonine can be produced by fermentation of strains of coryneform bacteria, in particular *Corynebacterium glutamicum*. On account of the great importance of L-threonine, attempts are constantly being made to improve the production processes. Production improvements may relate to fermentation technology measures such as for example stirring and provision of oxygen, or the composition of the nutrient medium such as for example the sugar concentration during fermentation, or the working-up to the product form by for example ion exchange chromatography, or the intrinsic production properties of the microorganism itself.

Methods employing mutagenesis, selection and choice of mutants are used to improve the production properties of these microorganisms. In this way strains are obtained that are resistant to antimetabolites such as for example the threonine analogon α-amino-β-hydroxyvaleric acid (AHV) or are auxotrophic for regulatory significant amino acids and produce L-threonine.

For some years now recombinant DNA technology methods have also been used for the strain improvement of L-threonine producing strains of Corynebacterium, by amplifying individual threonine biosynthesis genes and investigating the action on L-threonine production.

SUMMARY OF THE INVENTION

OBJECT OF THE INVENTION

The inventors have aimed to provide new measures for the improved enzymatic production of L-threonine.

DESCRIPTION OF THE INVENTION

L-threonine is used in animal nutrition, in human medicine and in the pharmaceutical industry. There is therefore a general interest in providing new improved processes for producing L-threonine.

The object of the invention is a preferably recombinant DNA derived from Corynebacterium and replicable in coryneform microorganisms, which contains at least the nucleotide sequence coding for the thrE gene, represented in the sequences SEQ-ID-No.1 and SEQ-ID-No.3.

The object of the invention is also a replicable DNA according to claim 1 with:

(i) the nucleotide sequences shown in SEQ-ID-No.1 or SEQ-ID-No.3, that code for the thrE gene, or (ii) at least one sequence that corresponds to the sequences (i) within the degeneration region of the genetic code, or (iii) at least one sequence that hybridises with the sequence complementary to the sequences (i) or (ii), and/or optionally (iv) functionally neutral sense mutations in (i).

The object of the invention are also coryneform microorganisms, in particular of the genus Corynebacterium, transformed by the introduction of the aforementioned replicable DNA.

The invention finally relates to a process for the enzymatic production of L-threonine using coryneform bacteria, which in particular already produce L-threonine and in which the nucleotide sequence(s) coding for the thrE gene is/are amplified, in particular overexpressed.

The term "amplification" describes in this connection the enhancement of the intracellular activity of one or more enzymes in a microorganism that are coded by the corresponding DNA, by for example increasing the copy number of the gene or genes or using a strong promoter or a gene that codes for a corresponding enzyme having a high activity, and if necessary using a combination of these measures.

The microorganisms that are the object of the present invention can produce L-threonine from glucose, sucrose, lactose, fructose, maltose, molasses, starch, cellulose or from glycerol and ethanol. The microorganisms may be representatives of coryneform bacteria, in particular of the genus Corynebacterium. In the genus Corynebacterium the species *Corynebacterium glutamicum* should in particular be mentioned, which is known to those in the specialist field for its ability to produce L-amino acids.

Suitable strains of the genus Corynebacterium, in particular of the species *Corynebacterium glutamicum,* are in particular the known wild type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-threonine-producing mutants or strains obtained therefrom, for example

*Corynebacterium glutamicum* ATCC21649
*Brevibacterium flavum* BB69
*Brevibacterium flavum* DSM5399
*Brevibacterium lactofermentum* FERM-BP 269
*Brevibacterium lactofermentum* TBB-10

The inventors have successfully managed to isolate the thrE gene of *Corynebacterium glutamicum.* In order to isolate the thrE gene a mutant of *C. glutamicum* defective in the thrE gene is first of all produced. To this end a suitable starting strain such as for example ATCC14752 or ATCC13032 is subjected to a mutagenesis process.

Conventional mutagenesis processes include treatment with chemicals, for example N-methyl-N-nitro-N-nitrosoguanidine, or UV irradiation. Such processes for initiating mutation are generally known and may be consulted in, inter alia, Miller (A Short Course in Bacterial Genetics, A Laboratory Manual and Handbook for *Escheri-*

*chia coli* and Related Bacteria (Cold Spring Harbor Laboratory Press, 1992)) or in the handbook "Manual of Methods for General Bacteriology" The American Society for Bacteriology (Washington D.C., USA, 1981).

Another mutagenesis process is the method of transposon mutagenesis in which the property of a transposon is utilised to "jump" in DNA sequences and thereby interfere with or switch off the function of the relevant gene. Transposons of coryneform bacteria are known in the specialist field. For example, the erythromycin resistance transposon Tn5432 (Tauch et al., Plasmid (1995) 33: 168–179) and the chloramphenicol resistance transposon Tn5546 have been isolated from *Corynebacterium xerosis* strain M82B.

Figure 1:
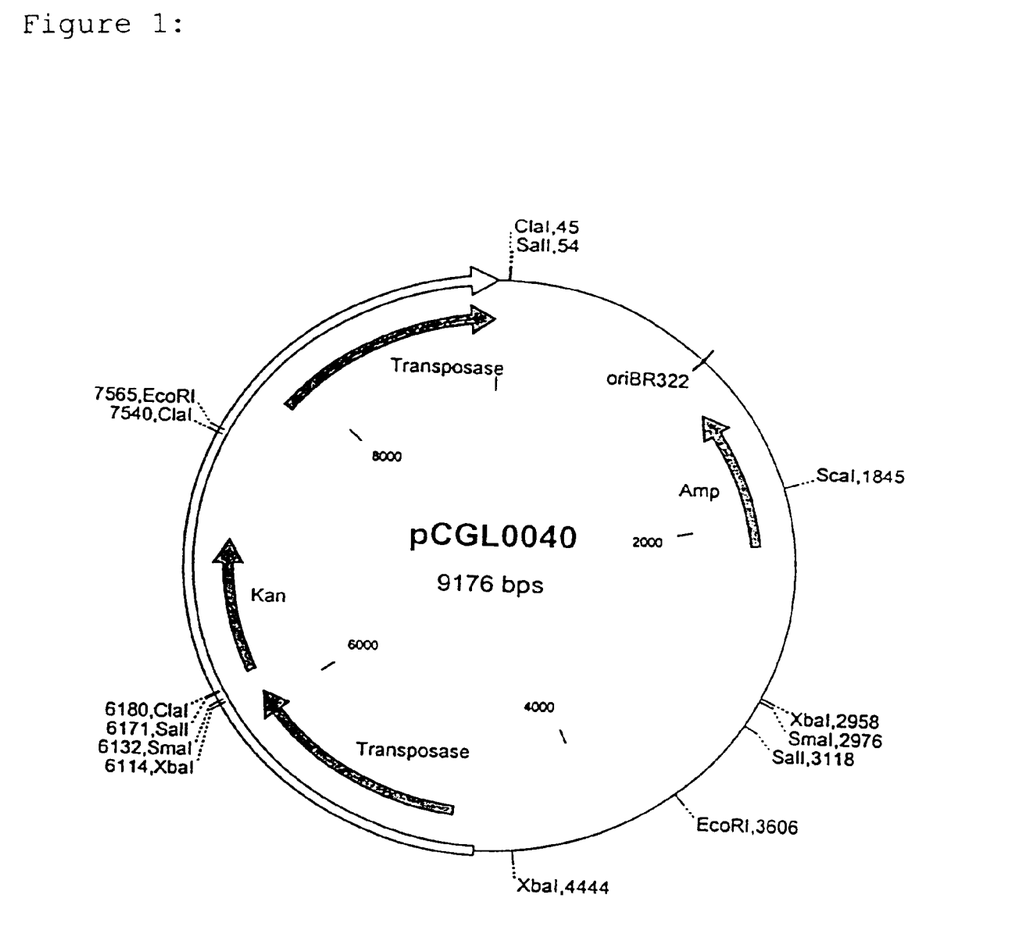
FIG. 1: Map of the plasmid pCGL0040 containing the transposon Tn5531. The transposon is characterised as a non-hatched arrow.

Another transposon is the transposon Tn5531 described by Ankri et al. (Journal of Bacteriology (1996) 178: 4412–4419) and that was used for example in the course of the present invention. The transposon Tn5531 contains the aph3 kanamycin resistance gene and can be delivered for example in the form of the plasmid vector pCGL0040, which is shown in FIG. 1. The nucleotide sequence of the transposon Tn5531 is freely available under the accession number U53587 from the National Center for Biotechnology Information (NCBI, Bethesda, Md., USA).

After mutagenesis, preferably transposon mutagenesis, has been carried out a search is made for a mutant defective in the thrE gene. A mutant defective in the thrE gene is recognised by the fact that it exhibits good growth on minimal agar, but poor growth on minimal agar that has been supplemented with threonine-containing oligopeptides, for example the tripeptide threonyl-threonyl-threonine.

An example of such a mutant is the strain ATCC14752ΔilvAthrE::Tn5531.

A strain produced in the described manner may be used to isolate and clone the thrE gene.

To this end a gene bank of the bacterium that is of interest may be established. The establishment of gene banks is recorded in generally known textbooks and manuals. There may be mentioned by way of example the textbook by Winnacker: Gene und Klone, eine Einfuhrung in die Gentechnologie (Gene and Clones, An Introduction to Gene Technology) (Verlag Chemie, Weinheim, Germany, 1990) or the manual by Sambrook et al.: Molecular Cloning, A Laboratory Manual (Cold Spring Harbor Laboratory Press, 1989). A very well-known gene bank is that of the *E. coli* K-12 strain W3110, which has been established by Kohara et al. (Cell 50, 495–508 (1987)) in λ-vectors. Bathe et al. (Molecular and General Genetics, 252:255–265, 1996) describes a gene bank of *C. glutamicum* ATCC13032, which has been established in the *E. coli* K-12 strain NM554 (Raleigh et al., 1988, Nucleic Acids Research 16:1563–1575) with the aid of the cosmid vector SuperCos I (Wahl et al., 1987, Proceedings of the National Academy of Sciences USA, 84:2160–2164). For the present invention those vectors are suitable that replicate in coryneform bacteria, preferably *Corynebacterium glutamicum*. Such vectors are known from the prior art; the plasmid vector pZ1 may be mentioned as an example, which is described by Menkel et al. (Applied and Environmental Microbiology (1989) 64: 549–554). The gene bank obtained in the described way is then converted by means of transformation or electroporation into the indicator strain defective in the thrE gene and those transformants are sought that have the ability to grow on minimal agar in the presence of threonine-containing oligopeptides. The cloned DNA fragment may then be subjected to a sequence analysis.

When using a mutant of a coryneform bacterium produced by Tn5531 mutagenesis, for example the strain ATCC14752ΔilvAthrE::Tn5531, the thrE::Tn5531 allele may be cloned directly using the kanamycin resistance gene aph3 contained in the latter and isolated. For this purpose known cloning vectors are used, such as for example pUC18 (Norrander et al., Gene (1983) 26: 101–106 and Yanisch-Perron et al., Gene (1985) 33: 103–119). Particularly suitable as cloning hosts are those *E. coli* strains that are both restriction-defective and recombinant-defective. An example is the strain DH5αmcr, which has been described by Grant et al. (Proceedings of the National Academy of Sciences USA, 87 (1990) 4645–4649). The selection for transformants is carried out in the presence of kanamycin. The plasmid DNA of the resultant transformants is then sequenced. For this purpose the dideoxy chain termination method described by Sanger et al. may be used (Proceedings of the National Academy of Sciences of the United States of America USA (1977) 74: 5463–5467). The thrE gene sequences upstream and downstream of the Tn5531 insertion site are thereby obtained. The resultant nucleotide sequences are then analysed and assembled with commercially available sequence analysis programs, for example with the program package Lasergene (Biocomputing Software for Windows, DNASTAR, Madison, USA) or the program package HUSAR (Release 4.0, EMBL, Heidelberg, Germany).

In this way the new DNA sequence of *C. glutamicum* coding for the thrE gene was obtained, which as SEQ ID NO 1 is a constituent part of the present invention. The amino acid sequence of the corresponding protein has also been derived from the present DNA sequence using the afore-described methods. The resulting amino acid sequence of the thrE gene product is represented in SEQ ID NO 2.

Coding DNA sequences that are produced from SEQ ID NO 1 by the degenerability of the genetic code are likewise a constituent part of the invention. In the same way, DNA sequences that hybridise with SEQ ID NO 1 or parts of SEQ ID NO 1 are a constituent part of the invention. Furthermore, conservative amino acid exchanges, for example the exchange of glycine by alanine or of aspartic acid by glutamic acid in proteins are known in the specialist field as sense mutations, which do not cause any fundamental change in the activity of the protein, i.e. are functionally neutral. It is furthermore known that changes at the N- and/or the C-terminus of a protein do not substantially affect its function or may even stabilise it. The person skilled in the art may find details of this in, inter alia, Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks on genetics and molecular biology. Amino acid sequences that are produced in a corresponding manner from SEQ ID NO 2 are likewise a constituent part of the invention.

Suitable primers can be synthesised using the nucleotide sequence shown in SEQ ID NO.1 and these are then used to amplify by means of the polymerase chain reaction (PCR) thrE genes of various coryneform bacteria and strains. The person skilled in the art may find details of this in for example the manual by Gait: Oligonucleotide synthesis: a practical approach (IRL Press, Oxford, UK, 1984) and in Newton and Graham: PCR (Spektrum Akademischer Verlag, Heidelberg, Germany, 1994). Alternatively, the nucleotide sequence shown in SEQ ID NO. 1 or parts thereof may be used as a probe to search for thrE genes in gene banks of in particular coryneform bacteria. The person skilled in the art can find details of this in for example the manual "The DIG System Users Guide for Filter Hybridization" published by Boehringer Mannheim GmbH (Mannheim, Germany, 1993) and in Liebl et al. (International Journal of Systematic Bacteriology (1991) 41: 255–260). The thrE gene-containing DNA fragments amplified in this way are then cloned and sequenced.

The DNA sequence of the thrE gene of the strain ATCC13032 illustrated in SEQ ID NO. 3 was obtained in this way, and is likewise a constituent part of the present invention. The resultant amino acid sequence is shown in SEQ ID NO. 4.

The invention also provides a process for isolating the thrE gene, characterised in that mutants, preferably of coryneform bacteria, defective in the thrE gene are obtained as indicator strains that do not grow or grow only weakly on a nutrient medium containing a threonine-containing oligopeptide, and a) the thrE gene is identified and isolated after establishing a gene bank, or b) in the case of transposon mutagenesis is selected for the transposon preferably exhibiting resistance to antibiotics, and the thrE gene is thereby obtained.

The inventors discovered from this that coryneform bacteria after over-expression of the thrE gene produce L-threonine in an improved manner In order to achieve an over-expression, the copy number of the corresponding genes can be increased, or the promoter and regulation region or the ribosome binding site located upstream of the structure gene can be mutated. Expression cassettes that are incorporated upstream of the structure gene work in the same way. It is in addition possible to enhance the expression during the course of the enzymatic L-threonine production by inducible promoters. The expression is also improved by measures aimed at lengthening the lifetime of the m-RNA. The enzymatic activity can also be increased by preventing the decomposition of the enzyme protein. The genes or gene constructs may be present either in plasmids with different copy numbers or may be integrated and amplified in the chromosome. Alternatively, an over-expression of the relevant genes can also be achieved by changing the composition of the culture media and cultivation conditions.

A person skilled in the art can find details of this in, inter alia, Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification EPS 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in Patent application WO 96/15246, in Malumbres et al. (Gene 134, 15–24 (1993)), in Japanese laid-open specification JP-A-10-229891, in Jensen and Hammer (Biotechnology and Bioengineering 58, 191–195 (1998)), in Makrides (Microbiological Reviews 60:512–538 (1996)) and in known textbooks on genetics and molecular biology.

An example of a plasmid by means of which the thrE gene can be overexpressed is pZ1thrE (FIG. 2), which is contained in the strain DM368–2 pZ1thrE. Plasmid pZ1thrE is a *C. glutamicum—E. coli* shuttle vector based on plasmid pZ1, which is described by Menkel et al. (Applied and Environmental Microbiology (1989) 64: 549–554). Other plasmid vectors replicable in *C. glutamicum*, such as for example pEKEx1 (Eikmanns et al., Gene 102:93–98 (1991)) or pZ8-1 (EP-B-0 375 889) can be used in the same way.

In addition, it may be advantageous for the production of L-threonine to over-express, in addition to the new thrE gene, one or more enzymes of the known threonine biosynthesis pathway or enzymes of the anaplerotic metabolism or enzymes of the citric acid cycle. The following may for example be simultaneously overexpressed:

the hom gene coding for homoserine dehydrogenase (Peoples et al., Molecular Microbiology 2, 63–72 (1988)) or the $hom^{dr}$ allele coding for a feedback-resistant homoserine dehydrogenase (Archer et al. Gene 107, 53–59, (1991)), or the pyc gene (DE-A-19 831 609) coding for pyruvate carboxylase, or the mqo gene coding for malate:quinone oxidoreductase (Molenaar et al., European Journal of Biochemistry 254, 39–403 (1998)).

For the production of L-threonine it may furthermore be advantageous, in addition to the over-expression of the thrE gene, to exclude undesirable secondary reactions, such as for example the threonine-dehydrogenase reaction (Nakayama: "Breeding of Amino Acid Producing Microorganisms", in: Overproduction of Microbial Products, Krumphanzl, Sikyta, Vanek (eds.), Academic Press, London, UK, 1982 and Bell and Turner, Biochemical Journal 156, 449–458 (1976)).

The microorganisms produced according to the invention may be cultivated continuously or batchwise in a batch process (batch cultivation) or in a fed batch (feed process) or repeated fed batch process (repetitive feed process) for the purposes of producing L-threonine. A summary of known cultivation methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Brunswick/Wiesbaden, 1994)).

The culture medium to be used must satisfy in an appropriate manner the requirements of the respective strains. Descriptions of culture media for various microorganisms are given in "Manual of Methods for General Bacteriology" The American Society for Bacteriology (Washington D.C., USA, 1981). Sources of carbon that may be used include sugars and carbohydrates, for example glucose, sucrose, lactose, fructose, maltose, molasses, starch and cellulose, oils and fats such as soybean oil, sunflower oil, groundnut oil and coconut oil, fatty acids such as palmitic acid, stearic acid and linoleic acid, alcohols such as glycerol and ethanol, and organic acids such as acetic acid. These substances may be used individually or as a mixture. Sources of nitrogen that may be used include organic compounds containing nitrogen such as peptones, yeast extract, meat extract, malt extract, corn steep liquor, soybean meal and urea, or inorganic compounds such as ammonium sulfate, ammonium chloride, ammonium phosphate, ammonium carbonate and ammonium nitrate. The sources of nitrogen may be used individually or as a mixture. Sources of phosphorus that may be used include phosphoric acid, potassium dihydrogen phosphate or dipotassium hydrogen phosphate, or the corresponding sodium salts. The culture medium must furthermore contain salts of metals such as for example magnesium sulfate or iron sulfate, which are necessary for growth. Finally, essential growth substances such as amino acids and vitamins may be used in addition to the aforementioned substances. Moreover, suitable precursors may be added to the culture medium. The aforementioned substances may be added to the culture in the form of a single batch or in an appropriate manner during the cultivation.

Basic compounds such as sodium hydroxide, potassium hydroxide, ammonia or ammonia water, or acidic compounds such as phosphoric acid or sulfuric acid may be added in an appropriate manner in order to control the pH of the culture. Anti-foaming agents such as for example fatty acid polyglycol esters may be used to control foam formation. Suitable selectively acting substances, for example antibiotics, may be added to the medium in order to maintain the stability of plasmids. Oxygen or oxygen-containing gas mixtures, for example air, may be fed into the culture to maintain aerobic conditions. The temperature of the culture is normally 20° C. to 45° C., and preferably 25° C. to 40° C. Cultivation is continued until a maximum amount of L-threonine has been formed. This target is normally achieved within 10 to 160 hours.

The analysis of L-threonine can be carried out by anion exchange chromatography followed by ninhydrin derivatisation as described by Spackman et al. (Analytical Chemistry, 30, (1958), 1190), or can be carried out by reversed phase HPLC as described by Lindroth et al. (Analytical Chemistry (1979) 51: 1167–1174).

The following microorganisms have been registered according to the Budapest Treaty at the German Collection for Microorganisms and Cell Cultures (DSMZ, Brunswick, Germany):

Brevibacterium flavum strain DM368-2 pZ1thrE as DSM 12840

Escherichia coli strain GM2929pCGL0040 as DSM 12839

DETAILED DESCRIPTION OF THE INVENTION

EXAMPLES

The present invention is described in more details hereinafter with the aid of examples of implementation.

The isolation of plasmid DNA from *Escherichia coli* as well as all techniques for restriction, Klenow and alkaline phosphatase treatment were carried out according to Sambrook et al. (Molecular cloning. A laboratory manual (1989) Cold Spring Harbour Laboratory Press). Unless otherwise specified, the transformation of *Escherichia coli* was carried out according to Chung et al. (Proceedings of the National Academy of Sciences of the United States of America USA (1989) 86: 2172–2175).

Example 1

Cloning and sequencing of the thrE gene of *Corynebacterium glutamicum* ATCC14752

1. Transposon Mutagenesis and Choice of Mutants

The strain *Corynebacterium glutamicum* ATCC14752ΔilvA was subjected to mutagenesis with the transposon Tn5531, whose sequence is filed under Accession No. U53587 in the Nucleotide Databank of the National Center for Biotechnology Information (Bethesda, USA). The incorporation of a deletion into the ilvA gene of *Corynebacterium glutamicum* ATCC14752 was carried out with the gene exchange system described by Schäfer et al. (Gene (1994) 145: 69–73). To this end, the inactivation vector pK19mobsacBΔilvA (Applied and Environmental Microbiology (1999) 65: 1973–1979) constructed by Sahm et al. was used for the deletion. The methylase-defective *Escherichia coli* strain SCS110 (Jerpseth and Kretz, STRATEGIES in molecular biology 6, 22, (1993)) from Stratagene (Heidelberg, Germany) was first of all transformed with 200 ng of the vector pK19mobsacBΔilvA. Transformants were identified by means of their kanamycin resistance on 50 μg/mL kanamycin-containing LB-agar plates. The plasmid pK19mobsacBΔilvA was prepared from one of the transformants. This inactivation plasmid was then introduced into the strain *Corynebacterium glutamicum* ATCC14752 by means of electroporation (Haynes et al., FEMS Microbiology Letters (1989) 61: 329–334). Clones in which the inactivation vector was present integrated in the genome were identified by means of their kanamycin resistance on 15 μg/mL kanamycin-containing LBHIS-agar plates (Liebl et al., FEMS Microbiology Letters (1989) 65: 299–304). In order to select for the excision of the vector, kanamycin-resistant clones were plated out on sucrose-containing LBG-Medium (LB-Medium with 15 g/L agar, 2% glucose and 10% sucrose). Colonies were obtained in this way which had lost the vector through a second recombination event (Jäger et al.; Journal of Bacteriology (1992) 174: 5462–5465). By hetero-inoculation on minimal medium plates (CGXII-Medium with 15 g/L agar (Keilhauer et al., Journal of Bacteriology (1993) 175: 5595–5603)) with and without 300 mg/L of L-isoleucine, and with and without 50 μg/mL of kanamycin, six clones were isolated that by excision of the vector were kanamycin sensitive and isoleucine auxotrophic and in which only the incomplete ilvA-Gen (ΔilvA allele) was present in the genome. One of these clones was designated strain ATCC14752ΔilvA and used for the transposon mutagenesis.

The plasmid pCGL0040, which contains the assembled transposon Tn5531 (Ankri et al., Journal of Bacteriology (1996) 178: 4412–4419) was isolated from the methylase-defective *E. coli* strain GM2929pCGL0040 (*E. coli* GM2929: Palmer et al., Gene (1994) 143: 1–12). The strain *Corynebacterium glutamicum* ATCC14752ΔilvA was transformed with the plasmid pCGL0040 by means of electroporation (Haynes et al., FEMS Microbiology Letters (1989) 61: 329–334). Clones in which the transposon Tn5531 was integrated into the genome were identified by means of their kanamycin resistance on 15 μg/mL kanamycin-containing LBHIS-agar plates (Liebl et al., FEMS Microbiology Letters (1989) 65: 299–304). In this way 2000 clones were obtained which were checked for retarded growth in the presence of threonyl-threonyl-threonine. For this purpose all clones were transferred individually to CGXII minimal medium agar plates with and without 2 mM threonyl-threonyl-threonine. The medium was identical to the medium CGXII described by Keilhauer et al. (Journal of Bacteriology (1993) 175: 5593–5603), but in addition contained 25 μg/mL of kanamycin, 300 mg/L of L-isoleucine and 15 g/L of agar. The composition of the medium described by Keilhauer et al. is shown in Table 1.

TABLE 1

Composition of the Medium CGXII

| Component | Concentration |
| --- | --- |
| $(NH_4)_2SO_4$ | 20 g/L |
| Urea | 5 g/L |
| $KH_2PO_4$ | 1 g/L |
| $K_2HPO_4$ | 1 g/L |
| $MgSO_4 \times 7\ H_2O$ | 0.25 g/L |
| 3-morpholinopropanesulfonic acid | 42 g/L |
| $CaCl_2$ | 10 mg/L |
| $FeSO_4 \times 7\ H_2O$ | 10 mg/L |
| $MnSO_4 \times H_2O$ | 10 mg/L |
| $ZnSO_4 \times 7H_2O$ | 1 mg/L |
| $CuSO_4$ | 0.2 mg/L |
| $NiCl_2 \times 6\ H_2O$ | 0.02 mg/L |
| Biotin | 0.2 mg/L |
| Glucose | 40 g/L |
| Protocatechuic Acid | 30 mg/L |

The agar plates were incubated at 30° C. and the growth was investigated after 12, 18 and 24 hours. A transposon mutant was obtained that grew in a comparable manner to the initial strain *Corynebacterium glutamicum* ATCC14752ΔilvA without threonyl-threonyl-threonine, but which in the presence of 2 mM threonyl-threonyl-threonine exhibited retarded growth. This was designated ATCC14752ΔilvAthrE::Tn5531.

2. Cloning and sequencing of the insertion site of Tn5531 in ATCC14752ΔilvAthrE::Tn5531.

In order to clone the insertion site located upstream of the transposon Tn5531 in the mutant described in Example 1.1, the chromosomal DNA of this mutant strain was first of all isolated as described by Schwarzer et al. (Bio/Technology (1990) 9: 84–87) and 400 ng of the latter was cut with the restriction endonuclease EcoRI. The complete restriction insert was ligated with the vector pUC18 likewise linearised with EcoRI (Norander et al., Gene (1983) 26: 101–106) from Roche Diagnostics (Mannheim, Germany). The *E. coli* strain DH5=mcr (Grant et al., Proceedings of the National Academy of Sciences of the United States of America USA (1990) 87: 4645–4649) was transformed with the complete ligation insert by means of electroporation (Dower et al., Nucleic Acid Research (1988) 16: 6127–6145). Transformants in which the insertion sites of the transposon Tn5531 were present cloned on the vector pUC18 were identified by means of their carbenicillin resistance and kanamycin resistance on LB-agar plates containing 50 μg/mL of carbenicillin and 25 μg/mL of kanamycin. The plasmids were prepared from three of the transformants and the sizes of the cloned inserts were determined by restriction analysis. The nucleotide sequence of the insertion site on one of the plasmids was determined with a ca. 5.7 kb large insert by the dideoxy chain termination method of Sanger et al. (Proceedings of the National Academy of Sciences of the United States of America USA (1977) 74: 5463–5467). For this purpose 2.2 kb of the insert were sequenced starting from the following oligonucleotide primer: 5'-CGG GTC TAC ACC GCT AGC CCA GG-3'.

In order to identify the insertion site located downstream of the transposon, the chromosomal DNA of the mutant was cut with the restriction endonuclease XbaI and ligated in the vector pUC18 linearised with XbaI. The further cloning was carried out as described above. The nucleotide sequence of the insertion site on one of the plasmids was determined with a ca. 8.5 kb large insert by the dideoxy chain termination method of Sanger et al. (Proceedings of the National Academy of Sciences of the United States of America USA (1977) 74: 5463–5467). For this purpose 0.65 kb of the insert was sequenced starting from the following oligonucleotide primer: 5'-CGG TGC CTT ATC CAT TCA GG-3'.

The obtained nucleotide sequences were analysed and assembled with the program package Lasergene (Biocomputing Software for Windows, DNASTAR, Madison, USA). This nucleotide sequence is reproduced as SEQ ID NO 1. The analysis identified an open reading frame 1467 bp long. The corresponding gene was designated the thrE gene. The associated gene product comprises 489 amino acids and is reproduced as SEQ ID NO 2.

Example 2

Cloning and Sequencing of the Gene thrE from *Corynebacterium glutamicum* ATCC13032

The gene thrE was cloned in the *E. coli* cloning vector pUC18 (Norrander et al., Gene (1983) 26: 101–106, Roche Diagnostics, Mannheim, Germany). The cloning was carried out in two stages. The gene from *Corynebacterium glutamicum* ATCC13032 was first of all amplified by a polymerase chain reaction (PCR) by means of the following oligonucleotide primer derived from SEQ ID NO 1

ThrE-forward: 5'-CCC CTT TGA CCT GGT GTT ATT G-3'
ThrE-reverse: 5'-CGG CTG CGG TTT CCT CTT-3'

The PCR reaction was carried out in 30 cycles in the presence of 200 μM of deoxynucleotide triphosphates (dATP, dCTP, dGTP, dTTP) and, for each, 1 μM of the corresponding oligonucleotide, 100 ng of chromosomal DNA from *Corynebacterium glutamicum* ATCC13032, 1/10 volumes of 10-fold reaction buffer and 2.6 units of a heat-stable Taq/Pwo-DNA polymerase mixture (Expand High Fidelity PCR System from Roche Diagnostics, Mannheim, Germany) in a Thermocycler (PTC-100, MJ Research, Inc., Watertown, USA) under the following conditions: 94° C. for 30 seconds, 58° C. for 30 seconds and 72° C. for 2 minutes.

The amplified, about 1.9 kb large fragment was then ligated using the SureClone Ligation Kit (Amersham Pharmacia Biotech, Uppsala, Sweden) according to the manufacturer's instructions, into the SmaI cleavage site of the vector pUC18. The *E. coli* strain DH5αmcr (Grant et al., Proceedings of the National Academy of Sciences of the United States of America USA (1990) 87: 4645–4649) was transformed with the whole ligation insert. Transformants were identified on the basis of their carbenicillin resistance on 50 μg/mL carbenicillin-containing LB agar plates. The plasmids were prepared from 8 of the transformants and tested by restriction analysis for the presence of the 1.9 kb PCR fragment as insert. The 25 resultant recombinant plasmid is designated hereinafter as pUC18thrE.

The nucleotide sequence of the 1.9 kb PCR fragment in plasmid pUC18thrE was determined by the dideoxy chain termination method of Sanger et al. (Proceedings of the National Academy of Sciences of the United States of America USA (1977) 74: 5463–5467). For this purpose the complete insert of pUC18thrE was sequenced with the aid of the following primers from Roche Diagnostics (Mannheim, Germany).

Universal primer: 5'-GTA AAA CGA CGG CCA GT-3'
Reverse primer: 5'-GGA AAC AGC TAT GAC CAT G-3'

The nucleotide sequence is reproduced as SEQ ID NO 3. The contained nucleotide sequence was analysed using the program package Lasergene (Biocomputing Software for Windows, DNASTAR, Madison, USA). The analysis identified an open reading frame 1467 bp long, which was designated the thrE gene. This codes for a polypeptide of 489 amino acids, which is reproduced as SEQ ID NO 4.

Example 3

Expression of the Gene thrE in *Corynebacterium glutamicum*

Figure 2:
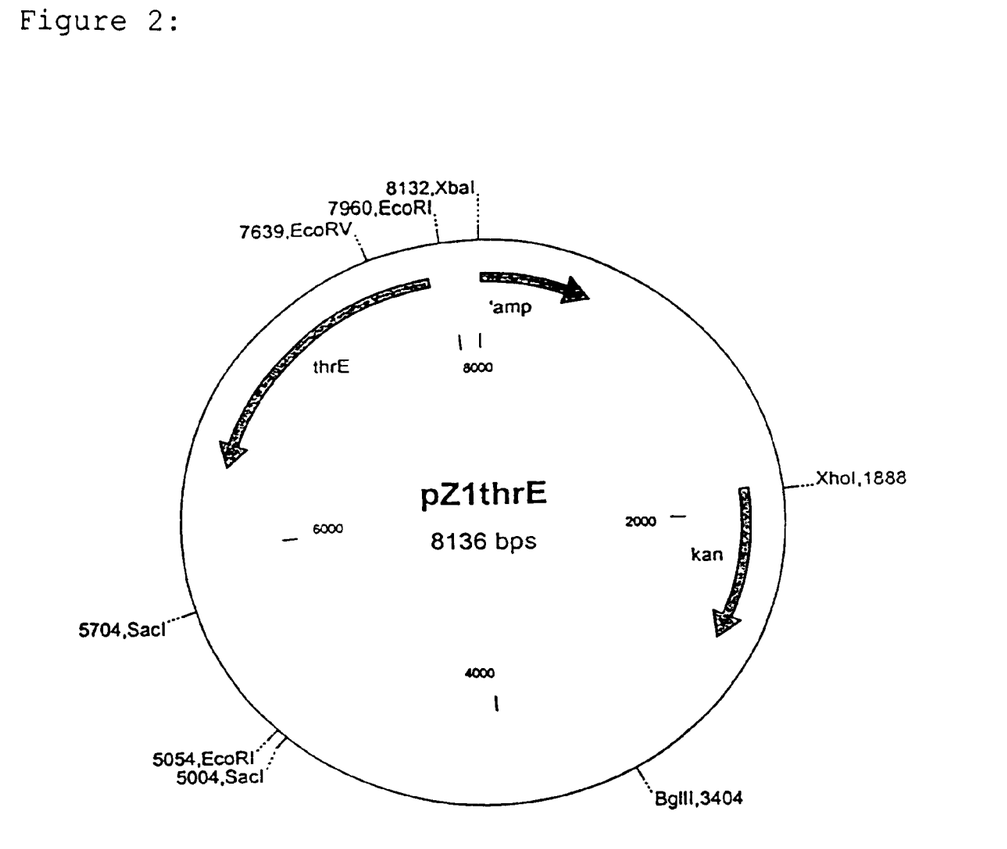
FIG. 2: Map of the plasmid pZ1thrE containing the thrE; gene.

The gene thrE from *Corynebacterium glutamicum* ATCC13032 described in Example 2 was cloned for expression in the vector pZ1(Menkel et al., Applied and Environmental Microbiology (1989) 64: 549–554). For this purpose a 1881 bp large DNA fragment containing the gene thrE was excised from the plasmid pUC18thrE using the restriction enzymes SacI and XbaI. The 5'- and 3'-ends of this fragment were treated with Klenow enzyme. The resulting DNA fragment was ligated in the vector pZ1 previously linearised and dephosphorylated with ScaI. The *E. coli* strain DH5αmcr (Grant et al., Proceedings of the National Academy of Sciences of the United States of America USA (1990) 87: 4645–4649) was transformed with the whole ligation insert. Transformants were identified on the basis of their kanamycin resistance on 50 μg/mL kanamycin-containing LB agar plates. The plasmids were prepared from two transformants and checked by restriction analysis for the presence of the 1881 bp ScaI/XbaI fragment as insert. The recombinant plasmid produced in this way was designated pZ1thrE (FIG. 2).

The plasmids pZ1 and pZ1thrE were incorporated by means of electroporation (Haynes et al., FEMS Microbiology Letters (1989) 61: 329–334) into the threonine-forming strain *Brevibacterium flavum* DM368-2. The strain DM368-2 is described in EP-B-0 385 940 and is filed as DSM5399. Transformants were identified on the basis of their kanamycin resistance on 15 μg/mL kanamycin-containing LBHIS-agar plates (Liebl et al., FEMS Microbiology Letters (1989) 65: 299–304). The strains *Brevibacterium flavum* DM368-2 pZ1 and DM368-2 pZ1thrE were obtained in this way.

Example 4
Preparation of L-threonine with *Brevibacterium flavum*

In order to investigate their threonine formation the strains *B. flavum* DM368-2 pZ1 and DM368-2 pZ1thrE were precultivated in 100 mL of brain heart infusion medium together with 50 μg of kanamycin/mL (Difco Laboratories, Detroit, USA) for 14 hours at 30° C. The cells were then washed once with 0.9%(w/v) of sodium chloride solution and 60 mL portions of CgXII medium were inoculated with this suspension so that the $OD_{600}$ (optical density at 600 nm) was 0.5. The medium was identical to the medium described by Keilhauer et al. (Journal of Bacteriology (1993) 175: 5593–5603), but contained in addition 50 μg of kanamycin per mL. Both strains were cultivated at 30° C. over a period of 72 hours. Samples were taken after 0, 24, 48 and 72 hours and the cells were quickly centrifuged off (5 minutes at 13000 RPM in a Biofuge pico from Heraeus, Osterode, Germany).

The quantitative determination of the extracellular amino acid concentrations from the culture supernatant was carried out by means of reversed phase HPLC (Lindroth et al., Analytical chemistry (1979) 51: 1167–1174). An HPLC apparatus of the HP1100 Series (Hewlett-Packard, Waldbronn, Germany) with attached fluorescence detector (G1321A) was used; the operation of the systems and the evaluation of the data was carried out with a HP-Chem-Station (Hewlett-Packard). 1 μL of the amino acid solution to be analysed was mixed in an automatic preliminary column derivatisation, step with 20 μL of o-phthalaldehyde/2-mercaptoethanol reagent (Pierce Europe BV, Oud-Beijerland, Netherlands).

The resultant fluorescing, thio-substituted isoindoles (Jones et al., Journal of Chromatography (1983) 266: 471–482) were separated in a combined preliminary column (40×4 mm Hypersil ODS 5) and main column (Hypersil ODS 5, both columns obtained from CS-Chromatographie Service GmbH, Langerwehe, Germany) using a gradient program with an increasingly non-polar phase (methanol).

The polar eluent was sodium acetate (0.1 molar, pH 7,2); the flow rate was 0.8 mL per minute. The fluorescence detection of the derivatised amino acids was carried out at an excitation wavelength of 230 nm and an emission wavelength of 450 nm. The amino acid concentrations were calculated by comparison with an external standard and asparagine as additional internal standard.

The results are shown in Table 2.

TABLE 2

| Strain | L-Threonine (g/L) | | | |
|---|---|---|---|---|
| | 0 Hrs. | 24 Hrs. | 48 Hrs. | 72 Hrs. |
| DM368-2 pZ1 | 0 | 0.46 | 1.27 | 1.50 |
| DM368-2 pZ1thrE | 0 | 0.68 | 1.71 | 2.04 |

BRIEF DESCRIPTION OF THE DRAWINGS

The results are accompanied by the following figures.

Length data should be regarded as approximate. The abbreviations and symbols employed have the following meaning.

BglII: restriction endonuclease from *Bacillus globigii*
EcoRi: restriction endonuclease from *Escherichia coli*
EcoRV: restriction endonuclease from *Escherichia coli*
SacI: restriction endonuclease from *Streptomyces achromogenes*
XbaI: restriction endonuclease from *Xanthomonas badrii*
XhoI: restriction endonuclease from *Xanthomonas holcicola*
Amp: ampicillin resistance gene
Kan: kanamycin resistance gene
'amp: 3' part of the ampicillin resistance gene
oriBR322: replication region of the plasmid pBR322

What is claimed is:

1. An isolated DNA molecule comprising a nucleotide sequence encoding a polypeptide comprising the amino acid sequence of either SEQ ID NO:2 or SEQ ID NO:4.

2. The isolated DNA molecule of claim 1, wherein said polypeptide consists of the amino acid sequence of SEQ ID NO:2.

3. The isolated DNA molecule of claim 1, wherein said polypeptide consists of the amino acid sequence of SEQ ID NO:4.

4. The DNA molecule of claim 1, wherein said DNA consists of a nucleotide sequence encoding the polypeptide of SEQ ID NO:2.

5. The DNA molecule of claim 1, wherein said DNA consists of a nucleotide sequence encoding the polypeptide of SEQ ID NO:4.

6. The isolated DNA of any one of claims 1–3, wherein said DNA is replicable in coryneform microorganisms.

7. A coryneform microorganism transformed with the DNA of any one of claims 1–5.

8. *Corynebacterium glutamicum* DM368-2 pZ1thrE, filed under accession number DSM 12840.

9. The isolated DNA molecule of claim 1, wherein said DNA molecule comprises the nucleotide sequence of either SEQ ID NO:1 or SEQ ID NO:3 and wherein said nucleotide sequence optionally has one or more functionally neutral sense mutations.

10. The isolated DNA molecule of claim 9, wherein said DNA molecule consists of the nucleotide sequence of SEQ ID NO:1 and optionally contains one or more functionally neutral sense mutations.

11. The isolated DNA molecule of claim 9, wherein said DNA molecule consists of the nucleotide sequence of SEQ ID NO:3 and optionally contains one or more functionally neutral sense mutations.

* * * * *

SEQUENCE LISTING

```
<160> NUMBER OF SEQ ID NOS: 4

<210> SEQ ID NO 1
<211> LENGTH: 2817
<212> TYPE: DNA
<213> ORGANISM: Corynebacterium glutamicum ATCC14752
<220> FEATURE:
<221> NAME/KEY: CDS
<222> LOCATION: (398)..(1864)
<223> OTHER INFORMATION: thrE-Gen

<400> SEQUENCE: 1
```

-continued

```
aatgaaataa tcccctcacc aactggcgac attcaaacac cgtttcattt ccaaacatcg      60
agccaaggga aaagaaagcc cctaagcccc gtgttattaa atggagactc tttggagacc     120
tcaagccaaa aagggcatt ttcattaaga aaatacccct ttgacctggt gttattgagc      180
tggagaagag acttgaactc tcaacctacg cattacaagt gcgttgcgct gccaattgcg     240
ccactccagc accgcagatg ctgatgatca caaactacga atacgtatct tagcgtatgt     300
gtacatcaca atggaattcg gggctagagt atctggtgaa ccgtgcataa acgacctgtg     360
attggactct ttttccttgc aaaatgtttt ccagcgg atg ttg agt ttt gcg acc      415
                                         Met Leu Ser Phe Ala Thr
                                           1               5 ctt cgt ggc cgc att tca aca gtt gac gct gca aaa gcc gca cct ccg       463
Leu Arg Gly Arg Ile Ser Thr Val Asp Ala Ala Lys Ala Ala Pro Pro
             10                  15                  20 cca tcg cca cta gcc ccg att gat ctc act gac cat agt caa gtg gcc       511
Pro Ser Pro Leu Ala Pro Ile Asp Leu Thr Asp His Ser Gln Val Ala
         25                  30                  35 ggt gtg atg aat ttg gct gcg aga att ggc gat att ttg ctt tct tca       559
Gly Val Met Asn Leu Ala Ala Arg Ile Gly Asp Ile Leu Leu Ser Ser
 40                  45                  50 ggt acg tca aac agt gat acc aag gtg caa gtt cga gcg gtg acc tct       607
Gly Thr Ser Asn Ser Asp Thr Lys Val Gln Val Arg Ala Val Thr Ser
 55                  60                  65                  70 gcg tat ggc ctg tac tat acg cat gtg gat atc acg ttg aat acg atc       655
Ala Tyr Gly Leu Tyr Tyr Thr His Val Asp Ile Thr Leu Asn Thr Ile
             75                  80                  85 acc atc ttc acc aac atc ggt gtg gag agg aag atg ccg gtc aac gtg       703
Thr Ile Phe Thr Asn Ile Gly Val Glu Arg Lys Met Pro Val Asn Val
         90                  95                 100 ttt cat gtt gtg ggc aag ttg gac acc aac ttc tcc aaa ctg tct gag       751
Phe His Val Val Gly Lys Leu Asp Thr Asn Phe Ser Lys Leu Ser Glu
     105                 110                 115 gtt gac cgt ttg atc cgt tcc att cag gct ggt gct acc ccg cct gag       799
Val Asp Arg Leu Ile Arg Ser Ile Gln Ala Gly Ala Thr Pro Pro Glu
120                 125                 130 gtt gcc gag aaa att ctg gac gag ttg gag caa tcg cct gcg tct tat       847
Val Ala Glu Lys Ile Leu Asp Glu Leu Glu Gln Ser Pro Ala Ser Tyr
135                 140                 145                 150 ggt ttc cct gtt gcg ttg ctt ggc tgg gca atg atg ggt ggc gct gtt       895
Gly Phe Pro Val Ala Leu Leu Gly Trp Ala Met Met Gly Gly Ala Val
             155                 160                 165 gct gtg ctg ttg ggt ggt gga tgg cag gtt tcc cta att gct ttt att       943
Ala Val Leu Leu Gly Gly Gly Trp Gln Val Ser Leu Ile Ala Phe Ile
         170                 175                 180 acc gcg ttc acg atc att gcc acg acg tca ttt ttg gga aag aag ggt       991
Thr Ala Phe Thr Ile Ile Ala Thr Thr Ser Phe Leu Gly Lys Lys Gly
     185                 190                 195 ttg cct act ttc ttc caa aat gtt gtt ggt ggt ttt att gcc acg ctg      1039
Leu Pro Thr Phe Phe Gln Asn Val Val Gly Gly Phe Ile Ala Thr Leu
200                 205                 210 cct gca tcg att gct tat tct ttg gcg ttg caa ttt ggt ctt gag atc      1087
Pro Ala Ser Ile Ala Tyr Ser Leu Ala Leu Gln Phe Gly Leu Glu Ile
215                 220                 225                 230 aaa ccg agc cag atc atc gca tct gga att gtt gtg ctg ttg gca ggt      1135
Lys Pro Ser Gln Ile Ile Ala Ser Gly Ile Val Val Leu Leu Ala Gly
             235                 240                 245 ttg aca ctt gtg caa tct ctg cag gac ggc atc acg ggc gct ccg gtg      1183
Leu Thr Leu Val Gln Ser Leu Gln Asp Gly Ile Thr Gly Ala Pro Val
         250                 255                 260
```

```
aca gca agt gca cga ttt ttt gaa aca ctc ctg ttt acc ggc ggc att        1231
Thr Ala Ser Ala Arg Phe Phe Glu Thr Leu Leu Phe Thr Gly Gly Ile
        265                 270                 275 gtt gct ggc gtg ggt ttg ggc att cag ctt tct gaa atc ttg cat gtc        1279
Val Ala Gly Val Gly Leu Gly Ile Gln Leu Ser Glu Ile Leu His Val
280                 285                 290 atg ttg cct gcc atg gag tcc gct gca gca cct aat tat tcg tct aca        1327
Met Leu Pro Ala Met Glu Ser Ala Ala Ala Pro Asn Tyr Ser Ser Thr
295                 300                 305                 310 ttc gcc cgc att atc gct ggt ggc gtc acc gca gcg gcc ttc gca gtg        1375
Phe Ala Arg Ile Ile Ala Gly Gly Val Thr Ala Ala Ala Phe Ala Val
                315                 320                 325 ggt tgt tac gcg gag tgg tcc tcg gtg att att gcg ggg ctt act gcg        1423
Gly Cys Tyr Ala Glu Trp Ser Ser Val Ile Ile Ala Gly Leu Thr Ala
            330                 335                 340 ctg atg ggt tct gcg ttt tat tac ctc ttc gtt gtt tat tta ggc ccc        1471
Leu Met Gly Ser Ala Phe Tyr Tyr Leu Phe Val Val Tyr Leu Gly Pro
        345                 350                 355 gtc tct gcc gct gcg att gct gca aca gca gtt ggt ttc act ggt ggt        1519
Val Ser Ala Ala Ala Ile Ala Ala Thr Ala Val Gly Phe Thr Gly Gly
    360                 365                 370 ttg ctt gcc cgt cga ttc ttg att cca ccg ttg att gtg gcg att gcc        1567
Leu Leu Ala Arg Arg Phe Leu Ile Pro Pro Leu Ile Val Ala Ile Ala
375                 380                 385                 390 ggc atc aca cca atg ctt cca ggt cta gca att tac cgc gga atg tac        1615
Gly Ile Thr Pro Met Leu Pro Gly Leu Ala Ile Tyr Arg Gly Met Tyr
                395                 400                 405 gcc acc ttg aat gat caa aca ctc atg ggt ttc acc aac att gcg gtt        1663
Ala Thr Leu Asn Asp Gln Thr Leu Met Gly Phe Thr Asn Ile Ala Val
            410                 415                 420 gct tta gcc act gct tca tca ctt gcc gct ggc gtg gtt ttg ggt gag        1711
Ala Leu Ala Thr Ala Ser Ser Leu Ala Ala Gly Val Val Leu Gly Glu
        425                 430                 435 tgg att gcc cgc agg cta cgt cgt cca cca cgc ttc aac cca tac cgt        1759
Trp Ile Ala Arg Arg Leu Arg Arg Pro Pro Arg Phe Asn Pro Tyr Arg
    440                 445                 450 gca ttt acc aag gcg aat gag ttc tcc ttc cag gag gaa gct gag cag        1807
Ala Phe Thr Lys Ala Asn Glu Phe Ser Phe Gln Glu Glu Ala Glu Gln
455                 460                 465                 470 aat cag cgc cgg cag aga aaa cgt cca aag act aat caa aga ttc ggt        1855
Asn Gln Arg Arg Gln Arg Lys Arg Pro Lys Thr Asn Gln Arg Phe Gly
                475                 480                 485 aat aaa agg taaaaatcaa cctgcttagg cgtctttcgc ttaaatagcg                1904
Asn Lys Arg tagaatatcg ggtcgatcgc ttttaaacac tcaggaggat ccttgccggc caaaatcacg      1964
gacactcgtc ccaccccaga atcccttcac gctgttgaag aggaaaccgc agccggtgcc      2024
cgcaggattg ttgccaccta ttctaaggac ttcttcgacg gcgtcacttt gatgtgcatg      2084
ctcggcgttg aacctcaggg cctgcgttac accaaggtcg cttctgaaca cgaggaagct     2144
cagccaaaga aggctacaaa gcggactcgt aaggcaccag ctaagaaggc tgctgctaag      2204
aaaacgacca agaagaccac taagaaaact actaaaaaga ccaccgcaaa gaagaccaca      2264
aagaagtctt aagccggatc ttatatggat gattccaata gctttgtagt tgttgctaac      2324
cgtctgccag tggatatgac tgtccaccca gatggtagct atagcatctc ccccagcccc      2384
ggtggccttg tcacggggct ttccccgtt ctggaacaac atcgtggatg ttgggtcgga       2444
tggcctggaa ctgtagatgt tgcacccgaa ccatttcgaa cagatacggg tgttttgctg      2504
```

-continued

```
cacctgttg tcctcactgc aagtgactat gaaggcttct acgagggctt ttcaaacgca    2564
acgctgtggc ctcttttcca cgatttgatt gttactccgg tgtacaacac cgattggtgg    2624
catgcgtttc gggaagtaaa cctcaagttc gctgaagccg tgagccaagt ggcggcacac    2684
ggtgccactg tgtgggtgca ggactatcag ctgttgctgg ttcctggcat tttgcgccag    2744
atgcgccctg atttgaagat cggtttcttc ctccacattc ccttcccttc ccctgatctg    2804
ttccgtcagc tgc                                                      2817
```

<210> SEQ ID NO 2
<211> LENGTH: 489
<212> TYPE: PRT
<213> ORGANISM: Corynebacterium glutamicum ATCC14752

<400> SEQUENCE: 2

```
Met Leu Ser Phe Ala Thr Leu Arg Gly Arg Ile Ser Thr Val Asp Ala
  1               5                  10                  15

Ala Lys Ala Ala Pro Pro Ser Pro Leu Ala Pro Ile Asp Leu Thr
             20                  25                  30

Asp His Ser Gln Val Ala Gly Val Met Asn Leu Ala Ala Arg Ile Gly
         35                  40                  45

Asp Ile Leu Leu Ser Ser Gly Thr Ser Asn Ser Asp Thr Lys Val Gln
     50                  55                  60

Val Arg Ala Val Thr Ser Ala Tyr Gly Leu Tyr Tyr Thr His Val Asp
 65                  70                  75                  80

Ile Thr Leu Asn Thr Ile Thr Phe Thr Asn Ile Gly Val Glu Arg
                 85                  90                  95

Lys Met Pro Val Asn Val Phe His Val Val Gly Lys Leu Asp Thr Asn
                100                 105                 110

Phe Ser Lys Leu Ser Glu Val Asp Arg Leu Ile Arg Ser Ile Gln Ala
            115                 120                 125

Gly Ala Thr Pro Pro Glu Val Ala Glu Lys Ile Leu Asp Glu Leu Glu
        130                 135                 140

Gln Ser Pro Ala Ser Tyr Gly Phe Pro Val Ala Leu Leu Gly Trp Ala
145                 150                 155                 160

Met Met Gly Gly Ala Val Ala Val Leu Leu Gly Gly Trp Gln Val
                165                 170                 175

Ser Leu Ile Ala Phe Ile Thr Ala Phe Thr Ile Ile Ala Thr Thr Ser
            180                 185                 190

Phe Leu Gly Lys Lys Gly Leu Pro Thr Phe Phe Gln Asn Val Val Gly
        195                 200                 205

Gly Phe Ile Ala Thr Leu Pro Ala Ser Ile Ala Tyr Ser Leu Ala Leu
    210                 215                 220

Gln Phe Gly Leu Glu Ile Lys Pro Ser Gln Ile Ala Ser Gly Ile
225                 230                 235                 240

Val Val Leu Leu Ala Gly Leu Thr Leu Val Gln Ser Leu Gln Asp Gly
                245                 250                 255

Ile Thr Gly Ala Pro Val Thr Ala Ser Ala Arg Phe Phe Glu Thr Leu
            260                 265                 270

Leu Phe Thr Gly Gly Ile Val Ala Gly Val Gly Leu Gly Ile Gln Leu
        275                 280                 285

Ser Glu Ile Leu His Val Met Leu Pro Ala Met Glu Ser Ala Ala Ala
    290                 295                 300

Pro Asn Tyr Ser Ser Thr Phe Ala Arg Ile Ile Ala Gly Gly Val Thr
```

-continued

```
                305                 310                 315                 320
Ala Ala Ala Phe Ala Gly Cys Tyr Ala Glu Trp Ser Ser Val Ile
                325                 330                 335

Ile Ala Gly Leu Thr Ala Leu Met Gly Ser Ala Phe Tyr Tyr Leu Phe
                340                 345                 350

Val Val Tyr Leu Gly Pro Val Ser Ala Ala Ile Ala Ala Thr Ala
                355                 360                 365

Val Gly Phe Thr Gly Gly Leu Leu Ala Arg Arg Phe Leu Ile Pro Pro
            370                 375                 380

Leu Ile Val Ala Ile Ala Gly Ile Thr Pro Met Leu Pro Gly Leu Ala
385                 390                 395                 400

Ile Tyr Arg Gly Met Tyr Ala Thr Leu Asn Asp Gln Thr Leu Met Gly
                405                 410                 415

Phe Thr Asn Ile Ala Val Ala Leu Ala Thr Ala Ser Ser Leu Ala Ala
                420                 425                 430

Gly Val Val Leu Gly Glu Trp Ile Ala Arg Arg Leu Arg Arg Pro Pro
                435                 440                 445

Arg Phe Asn Pro Tyr Arg Ala Phe Thr Lys Ala Asn Glu Phe Ser Phe
                450                 455                 460

Gln Glu Glu Ala Glu Gln Asn Gln Arg Arg Gln Arg Lys Arg Pro Lys
465                 470                 475                 480

Thr Asn Gln Arg Phe Gly Asn Lys Arg
                485
```

<210> SEQ ID NO 3
<211> LENGTH: 1909
<212> TYPE: DNA
<213> ORGANISM: Corynebacterium glutamicum ATCC13032
<220> FEATURE:
<221> NAME/KEY: CDS
<222> LOCATION: (280)..(1746)
<223> OTHER INFORMATION: thrE-Gen

<400> SEQUENCE: 3

```
agcttgcatg cctgcaggtc gactctagag gatccccccc ctttgacctg gtgttattga      60
gctggagaag agacttgaac tctcaaccta cgcattacaa gtgcgttgcg ctgccaattg     120
cgccactcca gcaccgcaga tgctgatgat caacaactac gaatacgtat cttagcgtat     180
gtgtacatca caatggaatt cggggctaga gtatctggtg aaccgtgcat aaacgacctg     240
tgattggact cttttccctt gcaaaatgtt ttccagcgg atg ttg agt ttt gcg        294
                                           Met Leu Ser Phe Ala
                                             1               5 acc ctt cgt ggc cgc att tca aca gtt gac gct gca aaa gcc gca cct       342
Thr Leu Arg Gly Arg Ile Ser Thr Val Asp Ala Ala Lys Ala Ala Pro
                 10                  15                  20 ccg cca tcg cca cta gcc ccg att gat ctc act gac cat agt caa gtg       390
Pro Pro Ser Pro Leu Ala Pro Ile Asp Leu Thr Asp His Ser Gln Val
             25                  30                  35 gcc ggt gtg atg aat ttg gct gcg aga att ggc gat att ttg ctt tct       438
Ala Gly Val Met Asn Leu Ala Ala Arg Ile Gly Asp Ile Leu Leu Ser
         40                  45                  50 tca ggt acg tca aat agt gac acc aag gta caa gtt cga gca gtg acc       486
Ser Gly Thr Ser Asn Ser Asp Thr Lys Val Gln Val Arg Ala Val Thr
     55                  60                  65 tct gcg tac ggt ttg tac tac acg cac gtg gat atc acg ttg aat acg       534
Ser Ala Tyr Gly Leu Tyr Tyr Thr His Val Asp Ile Thr Leu Asn Thr
 70                  75                  80                  85
```

-continued

| | |
|---|---|
| atc acc atc ttc acc aac atc ggt gtg gag agg aag atg ccg gtc aac<br>Ile Thr Ile Phe Thr Asn Ile Gly Val Glu Arg Lys Met Pro Val Asn<br>                    90                        95                  100 | 582 |
| gtg ttt cat gtt gta ggc aag ttg gac acc aac ttc tcc aaa ctg tct<br>Val Phe His Val Val Gly Lys Leu Asp Thr Asn Phe Ser Lys Leu Ser<br>                 105                    110                  115 | 630 |
| gag gtt gac cgt ttg atc cgt tcc att cag gct ggt gcg acc ccg cct<br>Glu Val Asp Arg Leu Ile Arg Ser Ile Gln Ala Gly Ala Thr Pro Pro<br>           120                    125                  130 | 678 |
| gag gtt gcc gag aaa atc ctg gac gag ttg gag caa tcc cct gcg tct<br>Glu Val Ala Glu Lys Ile Leu Asp Glu Leu Glu Gln Ser Pro Ala Ser<br>135                        140                  145 | 726 |
| tat ggt ttc cct gtt gcg ttg ctt ggc tgg gca atg atg ggt ggt gct<br>Tyr Gly Phe Pro Val Ala Leu Leu Gly Trp Ala Met Met Gly Gly Ala<br>150                        155                  160                  165 | 774 |
| gtt gct gtg ctg ttg ggt ggt gga tgg cag gtt tcc cta att gct ttt<br>Val Ala Val Leu Leu Gly Gly Gly Trp Gln Val Ser Leu Ile Ala Phe<br>                 170                    175                  180 | 822 |
| att acc gcg ttc acg atc att gcc acg acg tca ttt ttg gga aag aag<br>Ile Thr Ala Phe Thr Ile Ile Ala Thr Thr Ser Phe Leu Gly Lys Lys<br>                 185                    190                  195 | 870 |
| ggt ttg cct act ttc ttc caa aat gtt gtt ggt ggt ttt att gcc acg<br>Gly Leu Pro Thr Phe Phe Gln Asn Val Val Gly Gly Phe Ile Ala Thr<br>          200                    205                  210 | 918 |
| ctg cct gca tcg att gct tat tct ttg gcg ttg caa ttt ggt ctt gag<br>Leu Pro Ala Ser Ile Ala Tyr Ser Leu Ala Leu Gln Phe Gly Leu Glu<br>          215                    220                  225 | 966 |
| atc aaa ccg agc cag atc atc gca tct gga att gtt gtg ctg ttg gca<br>Ile Lys Pro Ser Gln Ile Ile Ala Ser Gly Ile Val Val Leu Leu Ala<br>230                        235                  240                  245 | 1014 |
| ggt ttg aca ctc gtg caa tct ctg cag gac ggc atc acg ggc gct ccg<br>Gly Leu Thr Leu Val Gln Ser Leu Gln Asp Gly Ile Thr Gly Ala Pro<br>                 250                    255                  260 | 1062 |
| gtg aca gca agt gca cga ttt ttc gaa aca ctc ctg ttt acc ggc ggc<br>Val Thr Ala Ser Ala Arg Phe Phe Glu Thr Leu Leu Phe Thr Gly Gly<br>                 265                    270                  275 | 1110 |
| att gtt gct ggc gtg ggt ttg ggc att cag ctt tct gaa atc ttg cat<br>Ile Val Ala Gly Val Gly Leu Gly Ile Gln Leu Ser Glu Ile Leu His<br>          280                    285                  290 | 1158 |
| gtc atg ttg cct gcc atg gag tcc gct gca gca cct aat tat tcg tct<br>Val Met Leu Pro Ala Met Glu Ser Ala Ala Ala Pro Asn Tyr Ser Ser<br>          295                    300                  305 | 1206 |
| aca ttc gcc cgc att atc gct ggt ggc gtc acc gca gcg gcc ttc gca<br>Thr Phe Ala Arg Ile Ile Ala Gly Gly Val Thr Ala Ala Ala Phe Ala<br>310                        315                  320                  325 | 1254 |
| gtg ggt tgt tac gcg gag tgg tcc tcg gtg att att gcg ggg ctt act<br>Val Gly Cys Tyr Ala Glu Trp Ser Ser Val Ile Ile Ala Gly Leu Thr<br>                 330                    335                  340 | 1302 |
| gcg ctg atg ggt tct gcg ttt tat tac ctc ttc gtt gtt tat tta ggc<br>Ala Leu Met Gly Ser Ala Phe Tyr Tyr Leu Phe Val Val Tyr Leu Gly<br>                 345                    350                  355 | 1350 |
| ccc gtc tct gcc gct gcg att gct gca aca gca gtt ggt ttc act ggt<br>Pro Val Ser Ala Ala Ala Ile Ala Ala Thr Ala Val Gly Phe Thr Gly<br>          360                    365                  370 | 1398 |
| ggt ttg ctt gcc cgt cga ttc ttg att cca ccg ttg att gtg gcg att<br>Gly Leu Leu Ala Arg Arg Phe Leu Ile Pro Pro Leu Ile Val Ala Ile<br>375                        380                  385 | 1446 |
| gcc ggc atc aca cca atg ctt cca ggt cta gca att tac cgc gga atg<br>Ala Gly Ile Thr Pro Met Leu Pro Gly Leu Ala Ile Tyr Arg Gly Met<br>390                        395                  400                  405 | 1494 |

```
tac gcc acc ctg aat gat caa aca ctc atg ggt ttc acc aac att gcg       1542
Tyr Ala Thr Leu Asn Asp Gln Thr Leu Met Gly Phe Thr Asn Ile Ala
                410                 415                 420 gtt gct tta gcc act gct tca tca ctt gcc gct ggc gtg gtt ttg ggt       1590
Val Ala Leu Ala Thr Ala Ser Ser Leu Ala Ala Gly Val Val Leu Gly
            425                 430                 435 gag tgg att gcc cgc agg cta cgt cgt cca cca cgc ttc aac cca tac       1638
Glu Trp Ile Ala Arg Arg Leu Arg Arg Pro Pro Arg Phe Asn Pro Tyr
                440                 445                 450 cgt gca ttt acc aag gcg aat gag ttc tcc ttc cag gag gaa gct gag       1686
Arg Ala Phe Thr Lys Ala Asn Glu Phe Ser Phe Gln Glu Glu Ala Glu
        455                 460                 465 cag aat cag cgc cgg cag aga aaa cgt cca aag act aat cag aga ttc       1734
Gln Asn Gln Arg Arg Gln Arg Lys Arg Pro Lys Thr Asn Gln Arg Phe
470                 475                 480                 485 ggt aat aaa agg taaaaatcaa cctgcttagg cgtctttcgc ttaaatagcg           1786
Gly Asn Lys Arg tagaatatcg ggtcgatcgc ttttaaacac tcaggaggat ccttgccggc caaaatcacg    1846
gacactcgtc ccaccccaga atcccttcac gctgttgaag aggaaaccgc agccggggta    1906
ccg                                                                   1909

<210> SEQ ID NO 4
<211> LENGTH: 489
<212> TYPE: PRT
<213> ORGANISM: Corynebacterium glutamicum ATCC13032

<400> SEQUENCE: 4

Met Leu Ser Phe Ala Thr Leu Arg Gly Arg Ile Ser Thr Val Asp Ala
  1               5                  10                  15

Ala Lys Ala Ala Pro Pro Ser Pro Leu Ala Pro Ile Asp Leu Thr
                 20                  25                  30

Asp His Ser Gln Val Ala Gly Val Met Asn Leu Ala Ala Arg Ile Gly
             35                  40                  45

Asp Ile Leu Leu Ser Ser Gly Thr Ser Asn Ser Asp Thr Lys Val Gln
         50                  55                  60

Val Arg Ala Val Thr Ser Ala Tyr Gly Leu Tyr Tyr Thr His Val Asp
 65                  70                  75                  80

Ile Thr Leu Asn Thr Ile Thr Ile Phe Thr Asn Ile Gly Val Glu Arg
                 85                  90                  95

Lys Met Pro Val Asn Val Phe His Val Val Gly Lys Leu Asp Thr Asn
                100                 105                 110

Phe Ser Lys Leu Ser Glu Val Asp Arg Leu Ile Arg Ser Ile Gln Ala
            115                 120                 125

Gly Ala Thr Pro Pro Glu Val Ala Glu Lys Ile Leu Asp Glu Leu Glu
        130                 135                 140

Gln Ser Pro Ala Ser Tyr Gly Phe Pro Val Ala Leu Leu Gly Trp Ala
145                 150                 155                 160

Met Met Gly Gly Ala Val Ala Val Leu Leu Gly Gly Trp Gln Val
                165                 170                 175

Ser Leu Ile Ala Phe Ile Thr Ala Phe Thr Ile Ala Thr Thr Ser
            180                 185                 190

Phe Leu Gly Lys Lys Gly Leu Pro Thr Phe Gln Asn Val Val Gly
        195                 200                 205

Gly Phe Ile Ala Thr Leu Pro Ala Ser Ile Ala Tyr Ser Leu Ala Leu
        210                 215                 220
```

```
Gln Phe Gly Leu Glu Ile Lys Pro Ser Gln Ile Ile Ala Ser Gly Ile
225                 230                 235                 240

Val Val Leu Leu Ala Gly Leu Thr Leu Val Gln Ser Leu Gln Asp Gly
                245                 250                 255

Ile Thr Gly Ala Pro Val Thr Ala Ser Ala Arg Phe Phe Glu Thr Leu
                260                 265                 270

Leu Phe Thr Gly Gly Ile Val Ala Gly Val Gly Leu Gly Ile Gln Leu
            275                 280                 285

Ser Glu Ile Leu His Val Met Leu Pro Ala Met Glu Ser Ala Ala Ala
        290                 295                 300

Pro Asn Tyr Ser Ser Thr Phe Ala Arg Ile Ile Ala Gly Gly Val Thr
305                 310                 315                 320

Ala Ala Ala Phe Ala Val Gly Cys Tyr Ala Glu Trp Ser Ser Val Ile
                325                 330                 335

Ile Ala Gly Leu Thr Ala Leu Met Gly Ser Ala Phe Tyr Tyr Leu Phe
            340                 345                 350

Val Val Tyr Leu Gly Pro Val Ser Ala Ala Ala Ile Ala Ala Thr Ala
            355                 360                 365

Val Gly Phe Thr Gly Gly Leu Leu Ala Arg Arg Phe Leu Ile Pro Pro
370                 375                 380

Leu Ile Val Ala Ile Ala Gly Ile Thr Pro Met Leu Pro Gly Leu Ala
385                 390                 395                 400

Ile Tyr Arg Gly Met Tyr Ala Thr Leu Asn Asp Gln Thr Leu Met Gly
                405                 410                 415

Phe Thr Asn Ile Ala Val Ala Leu Ala Thr Ala Ser Ser Leu Ala Ala
            420                 425                 430

Gly Val Val Leu Gly Glu Trp Ile Ala Arg Arg Leu Arg Arg Pro Pro
            435                 440                 445

Arg Phe Asn Pro Tyr Arg Ala Phe Thr Lys Ala Asn Glu Phe Ser Phe
        450                 455                 460

Gln Glu Glu Ala Glu Gln Asn Gln Arg Arg Gln Arg Lys Arg Pro Lys
465                 470                 475                 480

Thr Asn Gln Arg Phe Gly Asn Lys Arg
                485
```